United States Patent
Freier et al.

(10) Patent No.: US 12,263,185 B2
(45) Date of Patent: Apr. 1, 2025

(54) HEMOSTATIC MATERIAL AND SPRAY

(71) Applicant: BC3 Technologies, Inc., Baltimore, MD (US)

(72) Inventors: Thomas Freier, Rhineland-Palatinate (DE); Rivelino Montenegro, Rhineland-Palatinate (DE); Wayne Grube, Jr., Baltimore, MD (US)

(73) Assignee: BC3 TECHNOLOGIES, INC., Baltimore, MD (US)

( * ) Notice: Subject to any disclaimer, the term of this patent is extended or adjusted under 35 U.S.C. 154(b) by 141 days.

(21) Appl. No.: 16/266,170

(22) Filed: Feb. 4, 2019

(65) Prior Publication Data
US 2019/0240249 A1 Aug. 8, 2019

Related U.S. Application Data

(60) Provisional application No. 62/626,414, filed on Feb. 5, 2018.

(51) Int. Cl.
| | | |
|---|---|---|
| *A61K 31/722* | (2006.01) | |
| *A61K 9/00* | (2006.01) | |
| *A61K 9/12* | (2006.01) | |
| *A61K 9/14* | (2006.01) | |
| *A61K 9/70* | (2006.01) | |
| *A61K 47/36* | (2006.01) | |
| *A61L 15/00* | (2006.01) | |

(52) U.S. Cl.
CPC .......... *A61K 31/722* (2013.01); *A61K 9/0014* (2013.01); *A61K 9/12* (2013.01); *A61K 9/124* (2013.01); *A61K 9/146* (2013.01); *A61K 9/7015* (2013.01); *A61K 47/36* (2013.01); *A61L 15/00* (2013.01)

(58) Field of Classification Search
CPC .. A61L 26/0023; A61L 15/00; A61L 26/0076; C08L 5/08; A61K 31/722; A61K 47/36; A61K 9/0014; A61K 9/12; A61K 9/124; A61K 9/146; A61K 9/7015; A61K 33/06; A61K 33/14; A61K 35/12; A61K 35/14; A61K 9/70; A61K 47/30; A61K 9/0024; A61K 9/08; A61K 9/14; A61K 33/10; A61K 33/42; A61K 35/16; A61K 35/19; A61K 45/06; A61K 47/26; A61K 47/42; A61K 9/19; A61P 17/02; A61P 7/04; A61P 19/02; C08B 37/003
USPC ....................................................... 424/493
See application file for complete search history.

(56) References Cited

U.S. PATENT DOCUMENTS

| | | | |
|---|---|---|---|
| 4,394,373 A | 7/1983 | Malette et al. | |
| 7,981,872 B2 | 7/2011 | Hardy et al. | |
| 8,106,030 B2 | 1/2012 | Hardy et al. | |
| 2008/0145455 A1 | 6/2008 | Bedard | |
| 2009/0149422 A1* | 6/2009 | Hardy | A61L 15/44 514/55 |
| 2011/0052712 A1* | 3/2011 | Eaton | C08L 29/04 424/493 |
| 2016/0032180 A1* | 2/2016 | Agrawal | A61K 8/8176 507/219 |
| 2018/0154038 A1* | 6/2018 | Zbozien | A61L 26/0023 |

FOREIGN PATENT DOCUMENTS

CN 103536955 A * 1/2014

OTHER PUBLICATIONS

CN103536955A_translation (Year: 2014).*
Shigemasa, et al., "Applications of Chitlin and Chitosan for Biomaterials," Biotech. Genetic. Eng. Rev. 1996, vol. 13, pp. 383.
Kumar, "A Review of Chitlin and Chitosan Applications," React. Funct. Polym. 2000, 46(1), 1.
Singh, et al., "Biomedical Applications of Chitlin, Chitosan and Their Derivatives," J. Macromol. Sci. 2000, C40(1), 69.
Kheirabadi, et al., "Evaluation of Tropical Hemostatic Agents for Combat Wound Treatment", US Army Med Dep J 2011:25-37.
Bennett, et al., "Management of External Hemorrhage in Tactical Combat Casualty Care: Chitosan-based Hemostatic Guaze Dressings," TCCC Guidelines Change 13-05, 16, Apr. 2014.
Kheirabadi, B.S., Examination of a Chitosan Spray Powder (second generation). Efficacy to Control Parenchymal Hemorrhage in Normal and Coagulopathic Swine, Protocol: A-04-011 TS24, Mar. 15, 2014.

* cited by examiner

*Primary Examiner* — Audrea B Coniglio
*Assistant Examiner* — Audrea Buckley
(74) *Attorney, Agent, or Firm* — Paul D. Strain, Esq.; Strain & Strain PLLC (57) ABSTRACT

A hemostatic material and a method of treating a bleeding wound of a human or an animal include a hemostatic powder for application to the wound. The hemostatic powder comprises a first part consisting of a native chitosan base and a second part consisting of a chitosan salt, where the first and the second parts form the main component of the hemostatic powder, or at least 50% of a total weight of the hemostatic powder, and the second part forms a layer that at least partially coats the first part. The hemostatic powder may be provided in a hemostatic spray formulation that comprises a mixture of the hemostatic powder dispersed in a liquefied gas for release from a cannister onto the wound. A treatment method involves applying the hemostatic spray formulation directly to the wound. Other embodiments are also disclosed.

22 Claims, 8 Drawing Sheets

HEMOSTATIC MATERIAL AND SPRAY

REFERENCE TO PENDING PRIOR PATENT APPLICATION

The application claims the benefit under 35 U.S.C. 119(e) of U.S. Provisional Patent Application No. 62/626,414, filed Feb. 5, 2018 by Thomas Freier, Rivelino Montenegro, and Wayne Grube Jr. for "HEMOSTATIC SPRAY," which patent application is hereby incorporated herein by reference.

BACKGROUND

Each year, approx. 200,000 Americans lose their lives to trauma. After a traumatic injury, hemorrhage is responsible for over 35% of pre-hospital deaths and over 40% of deaths within the first 24 hours. A cascade of life-threatening medical conditions can hereby occur simultaneously: 1) hemorrhage; 2) impaired resuscitation; 3) shock; 4) inflammation; and 5) coagulopathy. Appropriate management of the massively bleeding trauma patient includes the early identification of bleeding sources followed by prompt measures to minimize blood loss, restore tissue perfusion, and achieve haemodynamic stability.

Severe bleeding wounds that cannot be treated with standard hemostatic methods also remain the number one cause of potentially preventable death among combat casualties. A review of lethal wounds in autopsy reports of combat deaths in Iraq and Afghanistan has revealed that nearly 24% of deaths could have been potentially prevented if early and effective treatments had been provided. Of those potentially preventable deaths, 85% were caused by uncontrolled hemorrhage. These findings emphasize the need for prompt and more effective hemorrhage control treatment in the field and in combat support hospitals.

The polysaccharide chitosan is the at least partially N-deacetylated derivative of chitin. Chitin can be found widely in the exoskeletons of arthropods, shells, crustaceans, and the cuticles of insects. Chitosan, in general, is synthetically prepared by hydrolysis of chitin, although it can also be naturally derived directly, for example, from certain fungi. The different solubilities of chitin and chitosan in dilute acids are commonly used to distinguish between the two polysaccharides. Chitosan, the soluble form, can have a degree of acetylation (DA) between 0% and about 60%, the upper limit depending on parameters such as processing conditions, molecular weight, and solvent characteristics. While soluble in acidic aqueous media, chitosan precipitates at a neutral or alkaline pH.

Both chitin and chitosan are promising polymers for biomedical applications because of their biocompatibility, biodegradability, and structural similarity to the glycosaminoglycans. Chitosan has been found to demonstrate strong hemostatic characteristics. The hemostatic activity of chitosan does not depend on any part of the normal blood coagulation cascade. Instead, the hemostatic activity can be controlled by the molecular weight, degree of acetylation, and particularly cationic properties of chitosan interfering with negatively charged molecules at the surface of red blood cells and inducing blood coagulation. The mechanism of hemostasis can be described as a mixture of chemical and mechanical (adherence) linkages to red blood cells and tissues, forming a physical barrier around the severed vessels. For comprehensive reviews of potential applications of chitin and chitosan, see, e.g., Shigemasa and Minami, "Applications of chitin and chitosan for biomaterials," Biotech. Genetic. Eng. Rev. 1996, 13, 383; Kumar, "A review of chitin and chitosan applications," React. Funct. Polym. 2000, 46(1), 1; and Singh and Ray, "Biomedical applications of chitin, chitosan and their derivatives," J. Macromol. Sci. 2000, C40(1), 69.

Chitosan-based products for hemorrhage control have been in use in the military since 2002 when the HemCon Bandage was distributed for controlling severe bleeding on the battlefield. Due to limitations in applicability of the solid foam-like product and inconsistent efficacy of the dressing, the HemCon Bandage has been replaced by alternate dressings, including the chitosan-based Celox powder. Development of more effective products continues, as Celox, due to its loose powder form, is difficult to apply, limiting its wide distribution and use on the battlefield as well as in civilian emergency care situations.

An existing method of achieving hemostasis in bleeding open wounds is described in U.S. Pat. No. 4,394,373 and comprises placing chitosan, including in powder form, in contact with the bleeding wound. No information on the properties and hemostatic efficacy of the chitosan powder is provided.

U.S. Patent Publication No. 2008/0145455 describes a method for promoting blood clotting by contacting a blood clot promoter with blood, where the blood clot promoter comprises a mixture of a hydrophilic polymer, including chitosan or a chitosan derivative, and an inorganic material. The mixture may be in the form of a free-flowing powder. The chitosan may consist of neutralized chitosan (i.e., chitosan base) or re-acetylated chitosan. No further details on the chitosan derivative are provided.

U.S. Patent Publication 2009/0149422 describes a hemostatic powder comprising a chitosan salt, where the chitosan salt comprises one or more of the group consisting of chitosan acetate, chitosan lactate, chitosan succinate, chitosan malate, chitosan sulphate, and chitosan acrylate, together with at least one medical surfactant. Chitosan salts are described as ideally suited for the hemostatic powder application. Furthermore, it has been stated that by adding inert material to the powder made of chitosan salt, the performance of the powder is enhanced. This finding is not supported by the experimental results provided in the patent publication, which indeed shows the opposite, i.e., that the addition of inert materials actually leads to a decrease in the hemostatic efficacy of chitosan salt.

The current market for hemostatic agents is estimated at approximately $4Bn worldwide. The majority of products currently in use are based on inferior chitosan mixtures or derivatives, gelatin, collagen, oxidized cellulose, and thrombin materials that are far from ideal in terms of their hemostatic efficacy, biocompatibility, handling and application properties, and costs. There is a high and increasing demand for novel, more efficient hemostatic materials and devices not only in military and civilian emergency care applications, but also in a variety of surgical treatments, particularly in the cardiovascular field.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a hemostatic material for application to a wound of a human or an animal. The hemostatic material may comprise at least a first part consisting of a native chitosan base and a second part consisting of a chitosan salt, where the second part forms a layer that at least partially coats the first part, and the first and the second parts form at least 50% of a total weight of the hemostatic material.

Another embodiment provides a hemostatic spray formulation for application to a bleeding wound of a person or an animal. The hemostatic spray formulation may include a hemostatic powder dispersed within a dispersion medium for packaging within and release from a canister onto the bleeding wound, where the hemostatic powder comprises a main component consisting of a plurality of native chitosan particles that are at least partially coated with a native chitosan salt.

Yet another embodiment provides a method of treating a bleeding wound of a human or an animal. The method may include applying a hemostatic material to the bleeding wound, where at least 50% of a total weight of the hemostatic material is formed from a native chitosan base that is at least partially coated with a chitosan salt.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

In the context of this disclosure, the term "native chitosan" refers to the defined chemical entity chitosan, which is a poly(N-acetyl-D-glucosamine-co-D-glucosamine) copolymer or a poly(D-glucosamine) homopolymer. Any cross-linked or otherwise chemically modified chitosan is considered a chitosan derivative, having different properties than native chitosan. In the context of this disclosure, the term "native chitosan" includes both a neutralized chitosan (i.e., chitosan base) and chitosan in the form of a chitosan salt, dissolved or undissolved. When the disclosure refers to "chitosan" in general, this can be native chitosan or any derivative of a poly(N-acetyl-D-glucosamine-co-D-glucosamine) copolymer or a poly(D-glucosamine) homopolymer, cross-linked and/or otherwise modified.

The expression "main component" with regard to a hemostatic material means that the native chitosan makes up at least 50% of a total weight of the hemostatic material. Thus, if the hemostatic material is provided as a powder to be applied to the wound, this powder is required to be made up of native chitosan by at least 50% by weight. In the case of a dispersion comprising a hemostatic powder dispersed in a dispersion medium for being applied in contact with a wound, the expression "main component" with regard to the constituent(s) other than the dispersion medium means that at least 50% by weight of the combination of all constituents other than the dispersion medium must be chitosan. Note that material the hemostatic material takes up from a wound, such as blood, is not considered a component of the hemostatic material.

Also, embodiments of the hemostatic material discussed herein exploit the fact that native chitosan, including chitosan salt, is dissolvable in aqueous media. The terms "dissolvable" and "dissolution" refer to a process of mass loss of a solid chitosan form without a molecular weight decrease (i.e., without decrease in polymer chain length) due to solubility in an aqueous environment. This is to be distinguished from "degradation," which is the process of molecular weight decrease due to depolymerization of chitosan. It can be achieved with the hemostatic material disclosed herein, which is at least partly dissolvable.

This disclosure details a hemostatic material and associated methods of use and manufacture, specifically relating to a hemostatic chitosan spray for being applied in contact with a bleeding wound of a human or an animal. Embodiments include a hemostatic material based on a main component of native chitosan, or in one embodiment, an improved hemostatic powder, as well as a dispersion including the hemostatic powder dispersed in a dispersion medium and a method of treating a bleeding wound with the disclosed hemostatic material or dispersion.

In a spray formulation, the disclosed hemostatic material has uniquely strong hemostatic efficacy, as the spray combines the advantages of easy application on different, three-dimensionally shaped wound architectures independent of environmental conditions with the properties of a non-toxic, non-irritant hemostatic material having a proven history in clinical applications, rendering the spray well suited for both battlefield and medical treatment centers.

Hemostatic Material

Figure 1:
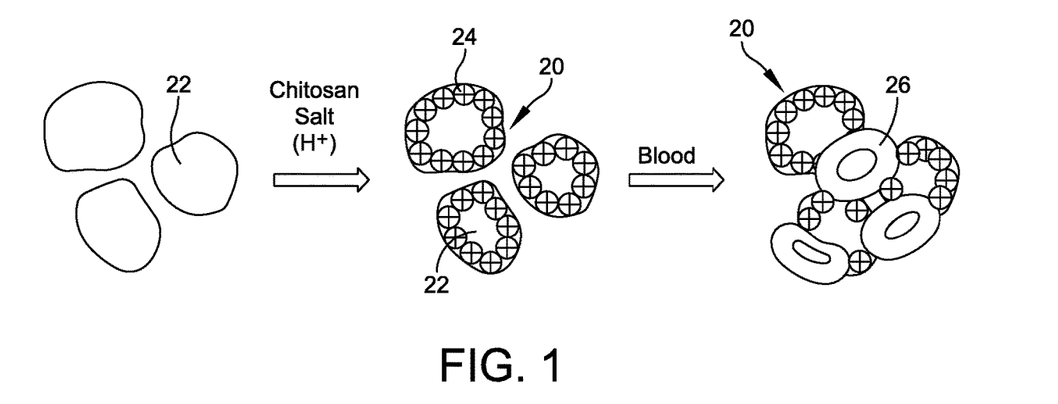
FIG. 1 provides a schematic depicting the components of one embodiment of a hemostatic material comprising a main component formed of a powder of native chitosan base, which is at least partially coated with a chitosan salt, and its interaction with blood cells.

Turning to the figures, FIG. 1 schematically illustrates one embodiment of a hemostatic material 20 for application in contact with a bleeding wound of a human or an animal and its interaction with blood cells 26, where the hemostatic material's main component, or at least 50% of a total weight of the hemostatic material, is formed of two parts: a first-part, or a native chitosan base 22, that is at least partially coated with a second-part, or a chitosan salt 24. In this embodiment, the chitosan salt 24 forms a layer that at least partially coats the native chitosan base 22, an inert material, by applying a surface modification reaction to the native chitosan base 22. As emphasized in FIG. 1, the hemostatic material 20 comprises the inert native chitosan base 22 that is surface-modified by the chitosan salt 24.

The disclosed hemostatic material 20 may take the form a hemostatic powder comprising an at least partially non-soluble part formed of the first part, or the native chitosan base 22, and a soluble part formed of the second part essentially consisting of the native chitosan salt 24. In this embodiment, the soluble part formed by the chitosan salt 24 forms a layer, which is at least partially coating the non-soluble part formed by the native chitosan base 22.

The hemostatic material 20 may be applied via a method of treating a bleeding wound of a human or an animal in which the hemostatic material 20 is applied in contact with the wound of the human or the animal, and the hemostatic material's main component is the native chitosan base 22 that is at least partially coated with the chitosan salt 24.

The hemostatic material 20 may be advantageously employed to achieve fast and efficient hemostasis of a bleeding wound, including improved hemostatic properties such as a reduced time to stop bleeding of the wound and a reduced amount of blood loss from the wound. Specifically, applying the native chitosan base 22 that is at least partially coated with the chitosan salt 24, as compared to applying a native chitosan base alone, a chitosan salt alone, or a physical mixture of a native chitosan base and a chitosan salt, achieves a significantly accelerated rate of hemostasis. This improved hemostasis is surprising considering the importance currently attributed to applying a native chitosan base, as described in U.S. Pat. No. 4,394,373, or in applying chitosan salts, as described in U.S. Patent Publication 2009/0149422, as hemostatic materials. Indeed, U.S. Patent Publication 2009/0149422 refers to physical mixtures of "inert materials" including insoluble chitosan (e.g., native chitosan) with chitosan salt which leads to a decreased hemostatic efficacy compared to applying chitosan salt alone.

Hemostatic Spray

Figure 2:
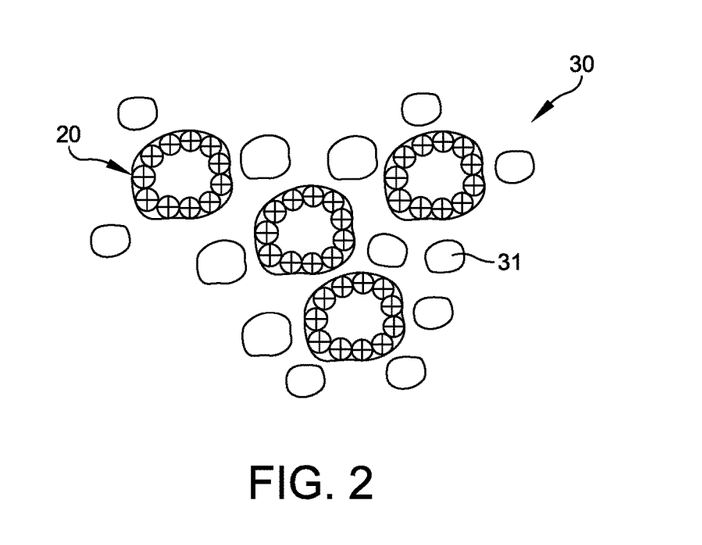
FIG. 2 provides a schematic depicting the components of one embodiment of a hemostatic spray formulation including the hemostatic material of FIG. 1.
Figure 3:
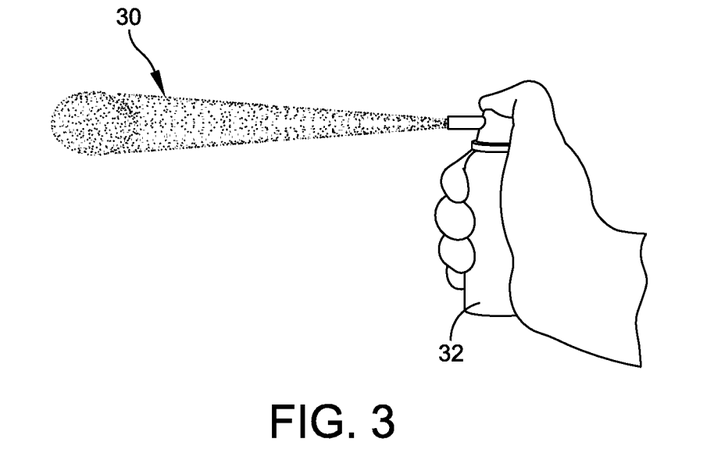
FIG. 3 illustrates the hemostatic spray formulation of FIG. 2, as released from a cannister.

As discussed above and in one embodiment, the hemostatic material 20, discussed above, may be provided in a sprayable formulation 30 (hereinafter "hemostatic spray," "spray formulation," "hemostatic chitosan spray," or "chitosan spray"), in which the activated hemostatic material/chitosan powder 20 is dispersed in a dispersion medium 31, such as a propellant, as shown in FIG. 2. The sprayable formulation 30 may be released from a can or a canister 32, as shown in FIG. 3. In one embodiment, the spray formulation 30 of the hemostatic material 20 may comprise a mixture of the chitosan powder 20 dispersed in a liquefied gas (e.g., propellant).

The sprayable formulation 30 packaged within the canister 32 may provide the additional benefit of vasoconstriction of blood vessels that further contributes to the quick stoppage of bleeding due to a short-term, but significant, decrease in temperature immediately after application, or upon a release of the hemostatic powder 20 from the spray can or canister 32 onto a surface of a bleeding wound. Existing hemostatic products fail to induce any vasoconstriction of blood vessels.

Notably, chitosan induces blood clotting by electrostatic interaction between the chitosan's positively charged glucosamine subunits and negatively charged blood cells. The disclosed hemostatic chitosan spray 30 has been formulated for maximum electrostatic potential and binding capacity towards blood cells. In one embodiment of the hemostatic chitosan spray 30, a low degree of acetylation (DA) of chitosan in the hemostatic material 20 results in a maximum availability of amine groups for physico-chemical interactions with blood or blood components. Deacetylation of chitosan to very low DA (high amine) values attributes to strong hemostatic activity, and a significant additional increase of the electrostatic (physico-chemical) interactions is achieved by transforming the amine groups into ammonium cationic moieties.

Figure 4:
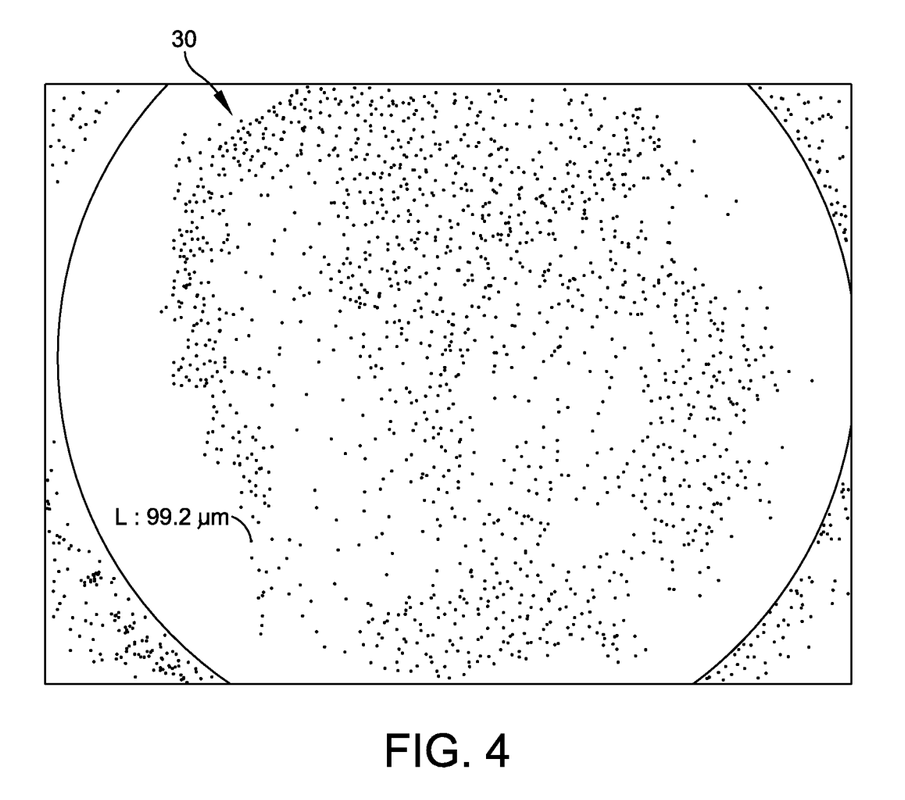
FIG. 4 illustrates a microscopic analysis of a particle size of the hemostatic spray formulation of FIGS. 2-3.
Figure 5:
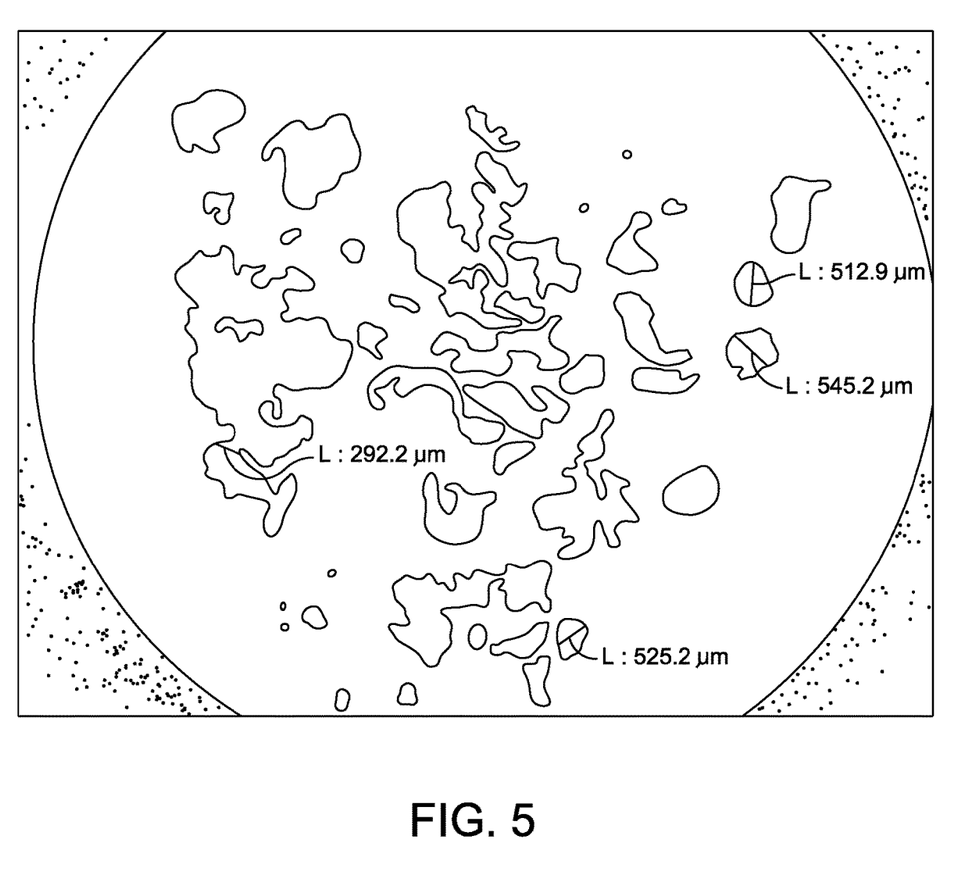
FIG. 5 illustrates a comparative microscopic analysis of a particle size of the prior art Celox powder.
Figure 6:
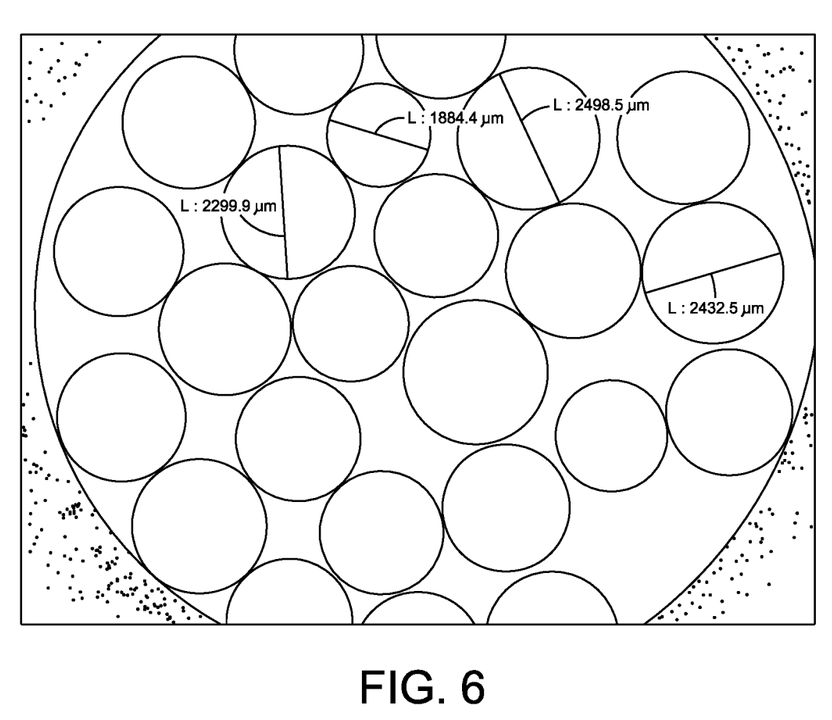
FIG. 6 illustrates a comparative microscopic analysis of a particle size of the prior art QuikClot product.
Figure 7:
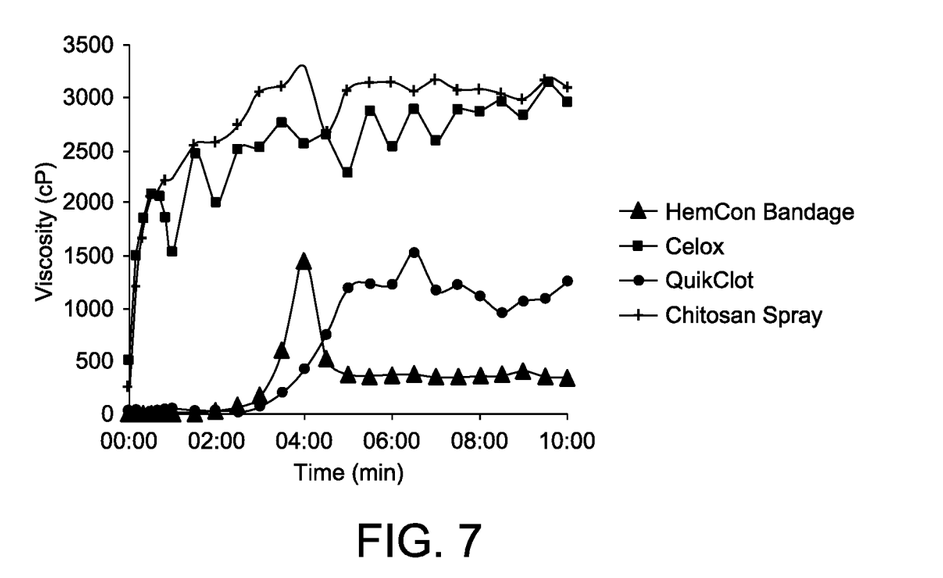
FIG. 7 provides a graphical representation of porcine blood viscosity after the addition of the existing HemCon Bandage, Celox, and QuikClot hemostatic products, as compared to the hemostatic spray formulation of FIGS. 2-3.

Further improved hemostatic activity is achieved through improved physico-chemical interactions due to the small particle size and high surface area of the hemostatic material 20 (i.e., the chitosan powder), which allows for maximum binding capacity with blood components, as discussed further below. That is, the hemostatic spray formulation 30 provides a high particle surface area, comprising a higher volume of smaller particles for maximum binding capacity between the oppositely charged components of the positively charged glucosamine subunits of the chitosan and the negatively charged blood cells, which improves physico-chemical interactions. Existing products, such as chitosan-based HemCon Bandage and Celox powder, as well as other products in use such as QuikClot, consist of a rather low particle surface area. A comparative analysis of the hemostatic activity of these products reveals the relationship between the particle surface area and coagulation times. For example, HemCon Bandage shows quicker blood stopping when provided in smaller pieces. The hemostatic spray formulation 30 contains significantly smaller particles than other products currently in the market, thus contributing to the strong hemostatic activity of this material. FIGS. 4-6 illustrate a comparative microscopic analysis of the particle diameter or cross-sectional length, L, of each of the disclosed hemostatic chitosan spray formulation 30 (<0.2 mm), and the prior art formulations Celox (0.2-1.0 mm) and QuikClot (1.8-2.5 mm), respectively, while FIG. 7 provides a graphical representation of a porcine blood viscosity after the addition of the existing prior art HemCon Bandage, Celox, and QuikClot products, as well as the disclosed hemostatic chitosan spray 30.

Figure 8:
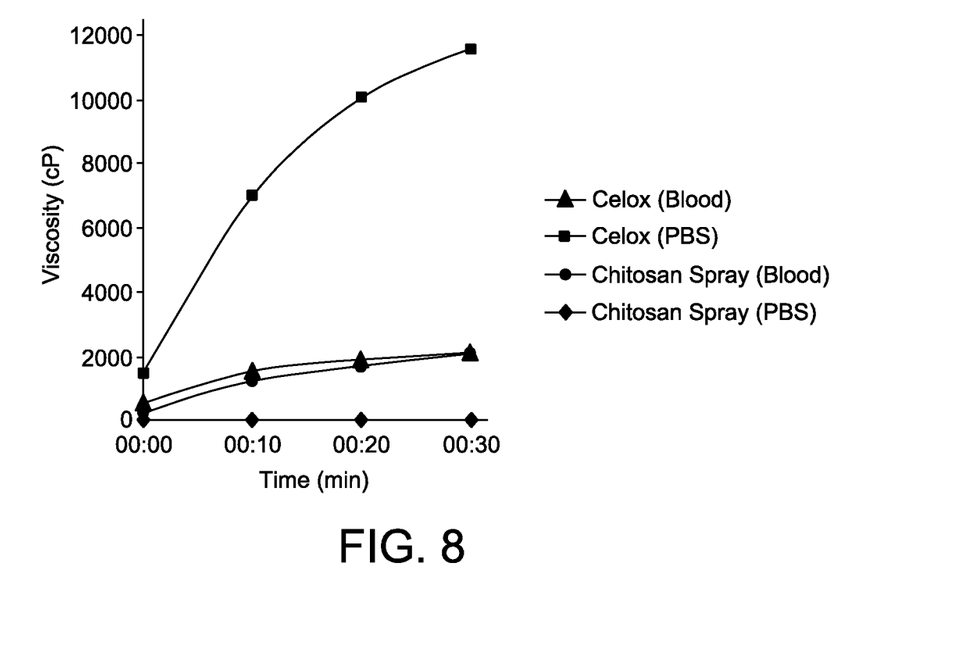
FIG. 8 provides a graph comparing the viscosity of porcine blood and a phosphate-buffered aqueous solution (PBS) after an addition of the prior art Celox powder and after an addition of the hemostatic spray formulation of FIGS. 2-3.

In addition, the hemostatic spray formulation 30 is active only in the presence of blood and experiences no change in consistency in the presence of plain water. Comparatively, the application of the existing formulation Celox results in the removal of liquid from any solution, leading to thickening and an increase in viscosity in both blood and a simple phosphate-buffered aqueous solution (PBS). Hence, any interaction of Celox with blood components, if existent, is superseded by the reaction with water. Thus, in the hemostatic spray formulation 30, the specific interaction of chitosan with blood components has been preserved and maximized. FIG. 8 provides a graph comparing the viscosity of porcine blood and PBS after the addition of Celox and after the addition the hemostatic chitosan spray 30. Notably, the PBS experienced no increase in viscosity after the addition of the hemostatic spray formulation 30. Only the blood experienced a viscosity increase after the addition of the chitosan spray 30, while the PBS experienced a dramatic viscosity increase after the addition of the prior art Celox powder.

The hemostatic spray formulation 30 also allows for the effective application of the product on three-dimensionally shaped wound architectures as is often observed in cases of trauma injuries. In contrast, solid foam-like materials, such as the HemCon Bandage and others existing in the prior art, cannot efficiently be applied to deep and uneven wounds and/or the complete coverage of these wounds is not possible. When compared to the existing powder product Celox, which is supplied as a powder to be poured from aluminum bags onto a wound, the hemostatic chitosan spray 30 allows for a precise application from a distance, which is particularly important for early intervention in cases where physical access to the injured person or animal remains restricted.

Moreover, the hemostatic chitosan spray 30 allows for the precise application of the hemostatic material/chitosan powder 20 in windy or other adverse conditions. In simulated windy conditions, a comparison between an application of the hemostatic spray formulation 30 and the existing Celox powder, revealed the spray formulation 30 to achieve a more precise application.

Figure 9A:
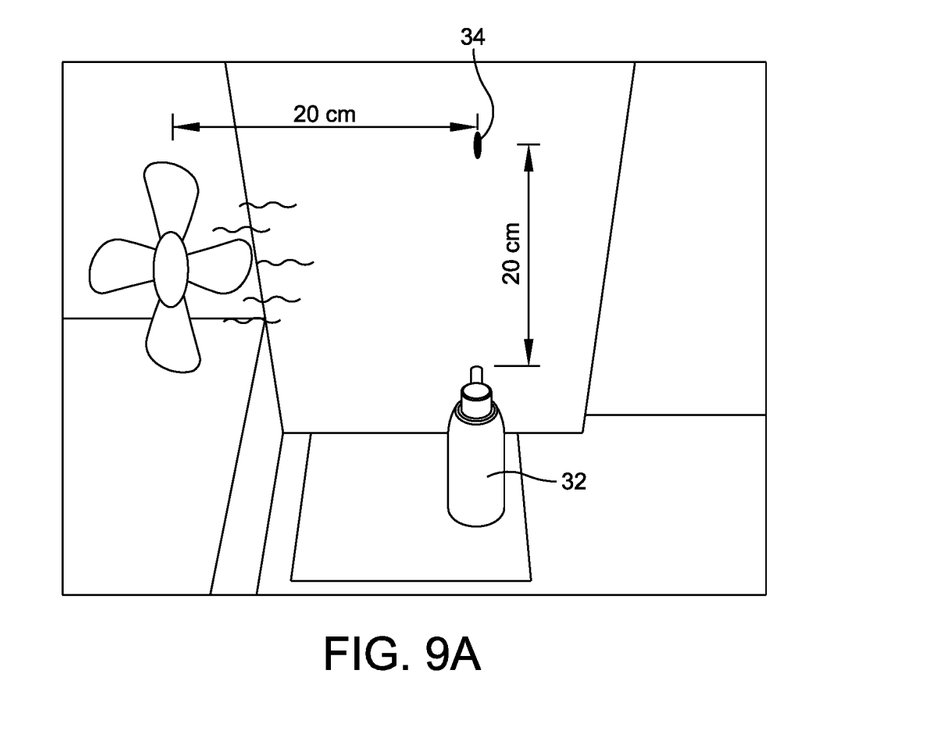
FIGS. 9A-9B illustrate perspective views of a simulated application of the hemostatic spray formulation of FIGS. 2-3, using a fan to simulate windy conditions.
Figure 9B:
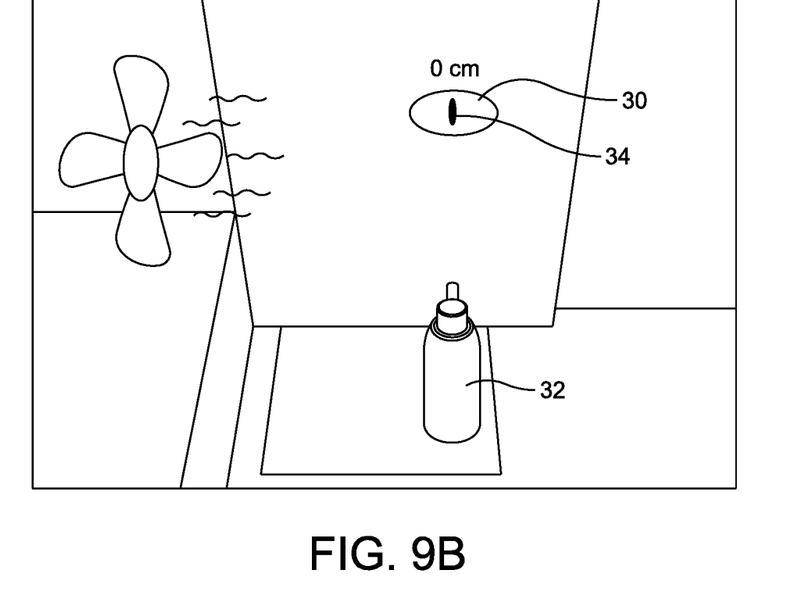
Figure 10A:
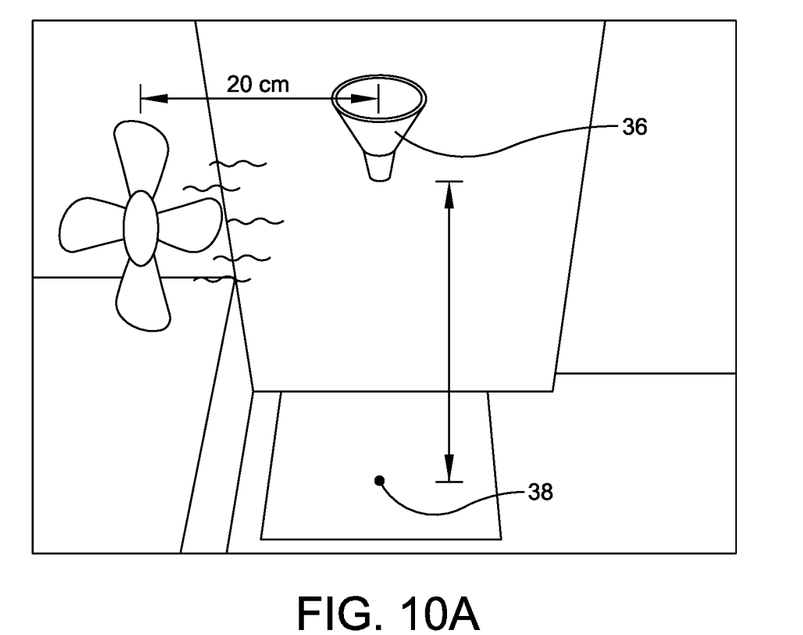
FIGS. 10A-10B illustrate respective perspective and top views of a simulated application of the prior art Celox powder using a fan to simulate windy conditions.
Figure 10B:
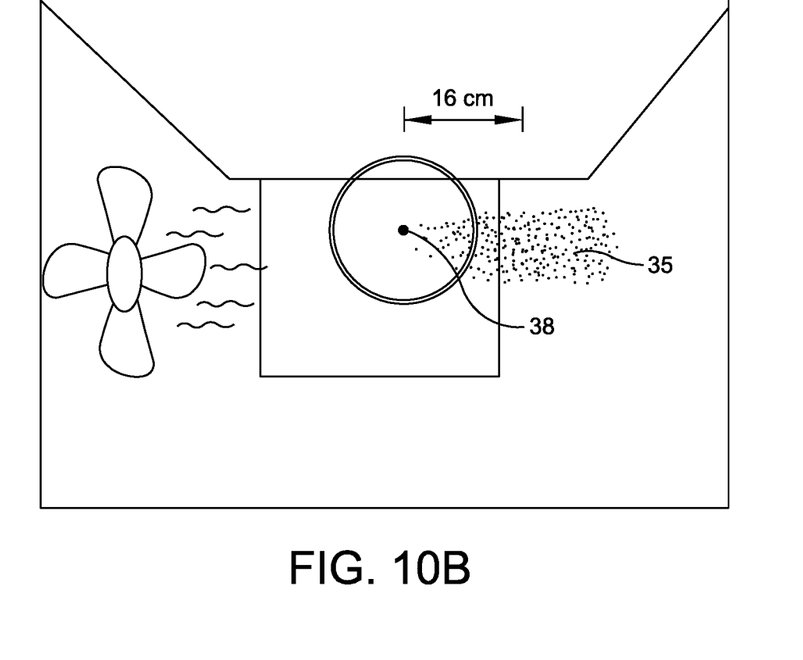

To demonstrate, FIGS. 9A-9B and 10A-10B provide a comparison between a simulated application of the disclosed hemostatic spray formulation 30 and a quantity 35 of the prior art Celox powder, respectively, using simulated windy conditions (e.g., a fan). For purposes of this experiment, the hemostatic spray formulation 30 was discharged from the cannister 32 at a distance of 20 cm from a targeted application center point 34, as shown in FIGS. 9A-9B, and the quantity 35 of the Celox powder was poured through a glass funnel 36 for this experiment at a height of 40 cm from a targeted application center point 38, as shown in FIGS. 10A-10B. Notably, the distance between the targeted application center point 34 and a center point of the applied material is 0 cm for the hemostatic spray formulation 30 (FIG. 9B), and the distance between the targeted application center point 38 and a center point of the applied material is 16 cm for the prior art Celox powder 35 (FIG. 10B).

Other attainable advantages of the hemostatic material 20, alone and dispersed within the hemostatic spray formulation 30, include the maintenance of a sufficient degree of humidity at the wound site, the absorption of exudative fluids and toxins, adequate gas exchange, and thermal insulation.

Figure 11A:
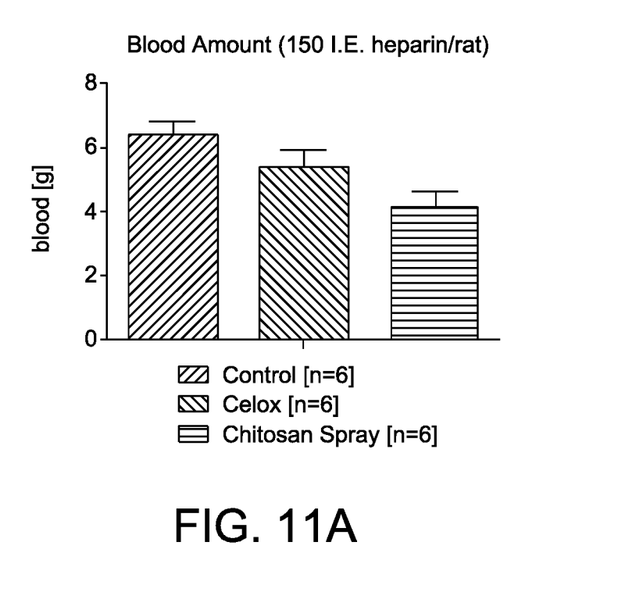
FIGS. 11A-11B graphically illustrate set of blood loss and bleeding time results, respectively, from in vivo testing in a rat liver resection model, comparing non-heparinized and heparinized animals in three groups including a non-treated group, a prior art Celox group, a group treated with the hemostatic spray formulation of FIGS. 2-3.
Figure 11B:
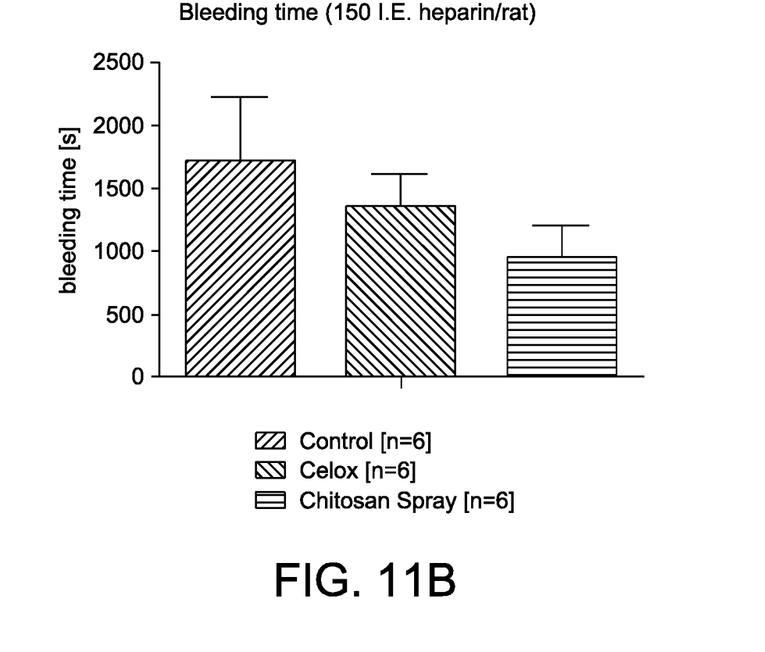

FIGS. 11A-11B graphically illustrate a set of respective blood loss and bleeding time results, respectively, from in vivo testing in a rat liver resection model, comparing non-heparinized and heparinized animals in three groups: Non-treated/control, treated with the prior art Celox powder, treated with the disclosed hemostatic chitosan spray 30. While all the non-heparinized animals survived, there were major differences between the heparinized groups: All animals from the non-treated, and all animals from the Celox-treated groups died within the first hour after start of the experiment. In contrast, two of the three animals of the group treated with the hemostatic chitosan spray 30 survived. The blood loss and bleeding time was significantly decreased for the hemostatic chitosan spray 30 group compared to the other groups.

Another experiment examined the applicability and efficacy of the hemostatic spray formulation 30, or the chitosan spray, to control parenchymal hemorrhage in a Grade III/IV liver injury model in swine. The wound closed well with chitosan adhesion and bleeding was stopped in the first hour of observation. The removal of gauze packs at 1 hour did not cause re-bleeding, and hemostasis remained secure during the second hour of monitoring. In contrast, treatment with standard absorbable Gelfoam used for comparison did not produce hemostasis and bleeding continued even after the liver was wrapped with additional gauze packs.

In summary, the disclosed hemostatic chitosan spray 30, formulated with the hemostatic material/chitosan powder 20, provides a number of innovative features compared to the currently used products for hemorrhage control, including (1) a novel highly active chitosan-based composition of material that provides long-term stability and prevents chitosan deactivation, with a significant additional increase in electrostatic, physico-chemical interactions achieved via deacetylation of chitosan to very low DA (high amine) values and by transforming the amine groups into ammonium cationic moieties; (2) usage of significantly smaller particles for maximization of hemostatic activity through improved physico-chemical interactions due to the high surface area of the chitosan powder that allows for maximum binding capacity with blood components; (3) formulation as a spray for precise application to deep and/or complex wound architectures from a distance and in windy conditions; and (4) short-term but significant application of cold resulting from a release of the hemostatic powder from the cannister onto the surface of the wound to induce vasoconstriction for facilitated hemostasis.

Figure 12:
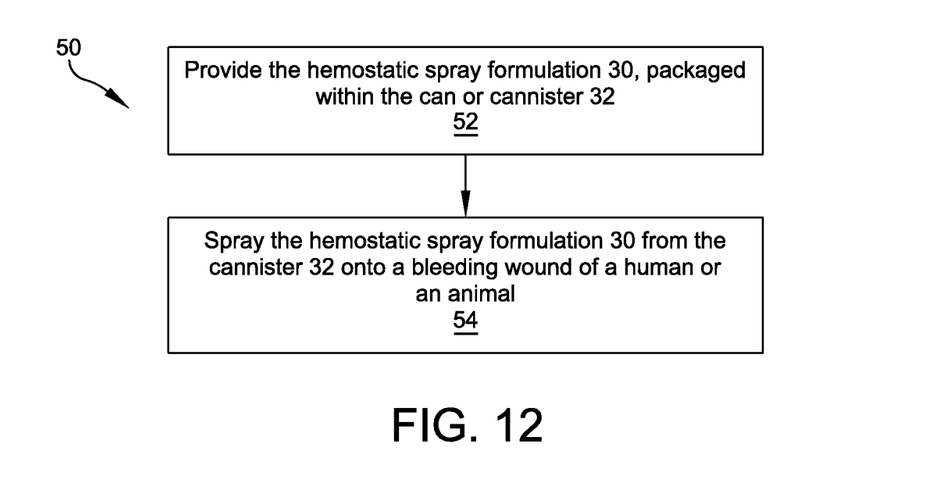
FIG. 12 provides a flowchart depicting an exemplary method of treating a bleeding wound of a human or an animal using the hemostatic spray formulation of FIGS. 2-3.

FIG. 12 provides a flowchart depicting an exemplary method (50) of treating a bleeding wound of a human or an animal using the hemostatic chitosan spray 30 described above. The method (50) may begin with providing the hemostatic spray formulation 30, packaged within the can or canister 32 (52). The hemostatic spray formulation 30 may be formed of the hemostatic material 20—in which the main component of the hemostatic material 20 is the native chitosan base 22 that is at least partially coated with the chitosan salt 24—dispersed within a dispersion medium such as a propellant. The method (50) may continue with applying (e.g., spraying) the hemostatic spray formulation 30 from the canister 32 onto a bleeding wound of a human or an animal (54). Applying the hemostatic spray formulation 30 (54) may occur from a distance and/or in adverse conditions (e.g., windy conditions, conditions in which the human or the animal are in motion such as, for instance, in the back of a moving vehicle, etc.).

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A hemostatic material for application to a wound of a human or an animal, the hemostatic material comprising at least a first part consisting of a native chitosan base and a second part consisting of a salt of the native chitosan base, wherein:
   the first part has a chemically modified surface which forms the second part as a surface layer thereon such that chitosan polymers of the first and second parts are interpenetrating and the first part is at least partially encapsulated by the second part, and the surface layer is configured to provide enhanced binding capacity with blood components as compared with a physical mixture of the native chitosan base and salt of the native chitosan base;
   the first part is at least partially non-soluble in water and the second part is at least partially soluble in water;
   the first and second parts are essentially non-soluble in blood; and
   the first and the second parts form at least 50% of a total weight of the hemostatic material.

2. The hemostatic material of claim 1, wherein the hemostatic material is provided as a hemostatic spray formulation that is released from a cannister in a spray form onto the wound.

3. The hemostatic material of claim 2, wherein the hemostatic spray formulation comprises a hemostatic powder dispersed in a liquefied gas.

4. The hemostatic material of claim 3, wherein the liquefied gas is a propellant.

5. The hemostatic material of claim 3, wherein releasing the hemostatic spray formulation from the cannister onto the wound causes a rapid decrease in temperature of the hemostatic powder and a short-term application of cold to the wound.

6. A hemostatic spray formulation for application to a bleeding wound of a person or an animal, comprising:
   a hemostatic powder dispersed within a dispersion medium for packaging within and release from a canister onto the bleeding wound, the hemostatic powder comprising a main component consisting of a plurality of native chitosan particles comprising the hemostatic material of claim 1,
   wherein the plurality of native chitosan particles provides the hemostatic powder with a larger surface area for enhanced binding capacity with blood components than a physical mixture of the native chitosan particles and the native chitosan salt,
   wherein the hemostatic powder is formed of individual particles, the plurality of particles having a mean diameter of less than 0.2 mm.

7. The hemostatic spray formulation of claim 6, wherein the dispersion medium comprises a propellant.

8. The hemostatic spray formulation of claim 6, wherein the hemostatic powder is active only in a presence of blood.

9. The hemostatic spray formulation of claim 6, wherein releasing the hemostatic spray formulation from the cannister onto the bleeding wound causes a rapid decrease in temperature of the hemostatic powder and a short-term application of cold to the wound, thereby inducing vasoconstriction of any blood vessels exposed at the bleeding wound.

10. A method of treating a bleeding wound of a human or an animal, the method comprising applying the hemostatic material according to claim 1 to the bleeding wound.

11. The method of claim 10, wherein the applying the hemostatic material comprises spraying a hemostatic spray formulation including the hemostatic material from a cannister onto the bleeding wound, thereby causing a rapid decrease in a temperature of the hemostatic material and inducing vasoconstriction in any exposed blood vessels at the bleeding wound.

12. The method of claim 11, wherein the hemostatic spray formulation comprises the hemostatic material dispersed in a liquefied gas.

13. The method of claim 11, wherein:
   the native chitosan base is at least partially non-soluble; and
   the chitosan salt is soluble.

14. The method of claim 10, wherein the native chitosan base that is at least partially coated with the chitosan salt has a low degree of acetylation to maximize a presence of amine groups in the hemostatic material to promote physico-chemical interactions between the hemostatic material and blood at the bleeding wound.

15. A hemostatic material for application to a wound of a human or an animal, the hemostatic material comprising:
   a plurality of particles, each comprising a core consisting of a native chitosan base, the native chitosan base being non-soluble in water, wherein:
   the core of each particle is modified with a surface layer comprising a salt of the native chitosan base, wherein the salt of the native chitosan base comprises a higher percentage of ammonium salt moieties as compared to the core, wherein the salt of the native chitosan base is at least partially soluble in water;
   the plurality of particles comprises at least 50% of the total weight of the hemostatic material,
   wherein the plurality of particles has a mean particle diameter less than 0.2 mm.

16. A hemostatic material for application to a wound of a human or an animal, the hemostatic material comprising:
   a plurality of functionalized particles, each comprising a native chitosan base, the native chitosan base being non-soluble in water, wherein:
   the native chitosan base comprises a surface modification wherein amine groups on the native chitosan backbone are at least partially transformed to ammonium cationic moieties such that the modified surface comprises a higher percentage of ammonium cationic moieties as compared to the core, wherein the modified surface at least partially coats the native chitosan base;
   the functionalized particles comprise at least 50% of the total weight of the hemostatic material,
   wherein the plurality of particles has a mean particle diameter less than 0.2 mm.

17. A particle comprising:
   a native chitosan base, the native chitosan base being non-soluble in water, and
   a modified surface, wherein the modified surface comprises a salt of the native chitosan base; and
   the particle has a diameter of less than 0.2 mm.

18. The hemostatic material of claim 1,
   wherein the native chitosan base has a low degree of acetylation to maximize a presence of amine groups for promoting physico-chemical interactions between the hemostatic material and blood at a bleeding wound.

19. The hemostatic material of claim 1,
   wherein the hemostatic material is not active in the presence of water but is active in the presence of blood.

20. The hemostatic material of claim 19,
   wherein the hemostatic material does not increase the viscosity of phosphate buffered saline solution (PBS).

21. The hemostatic material of claim 1, wherein the native chitosan base and salt thereof precipitates at a neutral or alkaline pH.

22. The hemostatic material of claim 1, wherein a hemostatic powder is formed of individual particles of the hemostatic material, wherein the plurality of particles has a mean diameter of less than 0.2 mm.

* * * * *